United States Patent [19]

Hennessy

[11] 4,167,038
[45] Sep. 4, 1979

[54] CALCULATED PARAMETER GENERATION IN A HEMATOLOGY PARAMETER MEASUREMENT APPARATUS

[75] Inventor: James W. Hennessy, Trumbull, Conn.

[73] Assignee: Hycel, Inc., Houston, Tex.

[21] Appl. No.: 842,508

[22] Filed: Oct. 17, 1977

[51] Int. Cl.² .................... G01N 27/00; G06F 15/42
[52] U.S. Cl. .................................. 364/416; 128/637; 235/92 PC; 324/71 CP; 364/555
[58] Field of Search ............. 364/416, 555; 128/2 G; 235/92 PC, 92 PL; 324/71 CP; 356/39

[56] References Cited

U.S. PATENT DOCUMENTS

| 3,973,189 | 8/1976 | Angel et al. ................. 364/416 X |
| 4,030,888 | 6/1977 | Yamamoto et al. ............ 356/39 X |
| 4,038,525 | 7/1977 | Freeman .................... 235/92 PL X |
| 4,052,596 | 10/1977 | Vick ............................. 128/2 G X |
| 4,063,309 | 12/1977 | Hennessy et al. ............ 364/416 X |
| 4,068,169 | 1/1978 | Angel et al. ................... 324/71 CP |

Primary Examiner—Jerry Smith
Attorney, Agent, or Firm—Robert P. Cogan

[57] ABSTRACT

In a hematology parameter measuring apparatus, signals indicative of measured parameters are obtained and loaded into first digital registers. Calculated parameter values are generated through use of the values stored in the digital registers. A first parameter value is circulated from a register into a digital divider through a digital data line to set a divisor in the divider. A control circuit circulates a value from another register to the divider for utilization as a signal indicative of a dividend. The output of the divider is coupled to a result register to store a value indicative of the calculated parameter. In this manner, calculated parameter values are obtained, and the first registers retain values indicative of the measured parameter values. The control means may selectively couple signals to a display from any of the registers or to a printing unit.

7 Claims, 3 Drawing Figures

CALCULATED PARAMETER GENERATION IN A HEMATOLOGY PARAMETER MEASUREMENT APPARATUS

BACKGROUND OF THE INVENTION

The present invention relates to hematology parameters measurement apparatus in which particle counting is performed and registers store results, and more particularly to such an apparatus in which hematology parameters are both measured and calculated.

The context contemplated for the present invention is the type of hematology parameter measuring apparatus in which a highly diluted blood sample is passed through an aperture in a conductivity sensor which produces a number of output pulses indicative of the number of blood cells in the blood sample. The apparatus further includes means for measuring hemoglobin by colorimetric analysis. An example of such an apparatus is disclosed in U.S. Pat. No. 3,921,066 to Henry R. Angle and James W. Hennessy, issued Nov. 18, 1975. This patent is now assigned to the assignee herein, and the disclosure thereof is incorporated herein by reference. Parameters measured by such apparatus include red blood count (RBC), white blood cells (WBC), and hemoglobin (HGB). It is also desirable to obtain values of further parameters such as hematocrit (HCT), which is the percentage by volume of a blood sample consistng of red blood cells. Hematocrit may be measured by totalizing the volume of red blood cells in a sample and multiplying or dividing by a scaling factor to account for blood sample volume. While this involves a calculation, for purposes of the present description, hematocrit is referred to as a measured parameter. An example of hematocrit measurement apparatus is disclosed in commonly assigned U.S. patent application Ser. No. 725,268 now U.S. Pat. No. 4,068,169 filed Sept. 21, 1976 by Henry R. Angel and Bernard O. Bachenheimer, the disclosure of which is incorporated herein by reference. It is also desirable to obtain indications of what are herein referred to as calculated values such as mean corpuscular volume (MCV). This is referred to as a calculated value herein because MCV may be calculated as hematocrit divided by RBC. An example of a circuit useful in the present type of hematology parameter measuring apparatus for providing a calculated value indicative of MCV is disclosed in U.S. patent application Ser. No. 723,805 now U.S. Pat. No. 4,063,309 filed Sept. 16, 1976 by James W. Hennessy and Bruce M. Turner, the disclosure of which is incorporated herein by reference. Further, calculated parameters which are useful in clinical diagnosis are mean corpuscular hemoglobin (MCH) and mean corpuscular hemoglobin concentration (MCHC).

It is desirable to provide an apparatus in which sensed signals produced by transducer apparatus are conveniently and efficiently handled to produce output signals indicative of both measured and calculated parameters. It is also necessary that such signal be provided to utilization means so that the results may be obtain by an operator for interpretation by a pathologist. In one particularly widely used form of prior art apparatus, parameters are produced within circuitry with certain parameters values being available for viewing by an opertor on a display and with all parameter values being provided to utilization means, particularly a printer providing visible numerical indications on a print card. It is desirable to provide a system in which a technician may examine all parameters first to determine, for example, whether or not to rerun a test before engaging in the time and expense of producing a printed card.

Most importantly, it is desired to provide circuitry for registering the measured values and for producing the calculated values which is simplified in construction and efficient in operation compared to prior apparatus.

SUMMARY OF THE INVENTION

It is therefore an object of the present invention to provide an automatic hematology parameter measuring apparatus for registering measured values and producing calculated values indicative of further parameters which is efficient both in construction and operation.

It is a further object of the invention to provide apparatus of the type described in which signals indicative of calculated and measured values may be supplied through utilization means, while providing for means to retain indications of said values in registers.

It is also an object of the present invention to provide an improved method for utilizing outut signals indicative of measured parameters in a hematology parameter apparatus to provide output indications of calculated parameters.

Briefly stated, in accordance with the present invention, there is provided a hematology parameter measurement apparatus in which prior art means provide signals having values indicative of measured parameters to register means. In order to produce values indicative of calculated parameters, the measured parameter values are selectively and individually accessed from their registers in a predetermined sequence. A first parameter is circulated into a digital divider through a data line to set a divisor in the divider circuit, and the value is recirculated into the register from which it came. The control circuit then selects the next register, and a pulse count is accessed therefrom having a value indicative of the value of that parameter and supplied to the digital divider as a dividend. The pulse count is also supplied again to the register from which it came. The divider provides an output indicative of the calculated parameter which may be delivered to a result register for provision for utilization means. For example, to obtain MCV, a pulse count indicative of RBC is counted into the digital divider and a pulse count indicative of hematocrit is next supplied to the digital divider. Outputs from the measured parameter value registers and the result registers are selectively connected to desired utilization means.

BRIEF DESCRIPTION OF THE DRAWINGS

The means by which the foregoing object and features of invention are achieved are pointed out with particularity in the claims forming the concluding portion of the specification. The invention, both as to its organization and manner of operation, may be further understood by reference to the following description taken in connection with the following drawings.

Of the Drawings.

DESCRIPTION OF THE PREFERRED EMBODIMENT

Figure 1:
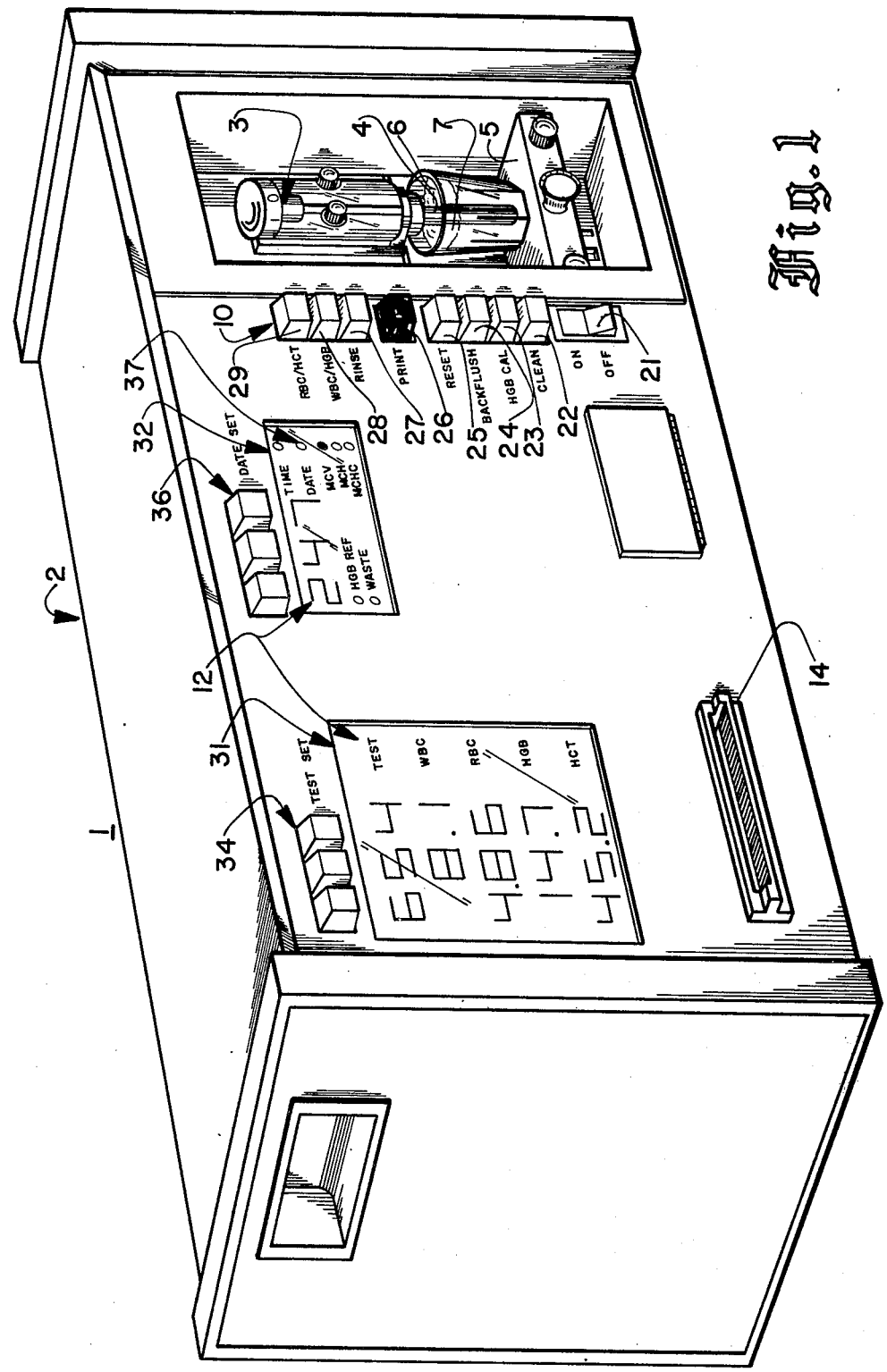
FIG. 1 is an illustration of a hematology parameter measurement apparatus incorporating the present invention.

Referring to FIG. 1, there is illustrated a hematology parameter measuring apparatus 1 constructed in accordance with the present invention. The apparatus 1 includes a housing 2 having mounted therein a conductivity sensor 3, which includes a probe 4 having an aperture. A carriage 5 is mounted below the sensor 3 for receiving a sample cup 7 which holds a highly diluted sample 6. The carriage 5 is movable so that the probe 4 is immersed in the sample dilution 6, and draws the dilution 6 therethrough for counting of cells by the sensor 3. The apparatus 1 is briefly described here, and further details relating to prior art aspects thereof may be found, for example, in the above cited patent to Angel et al. Control circuitry, further described below, synchronizes necessary operations in response to function selection by an operator achieved through depression of one of a plurality of function selection buttons 10. Results obtained may be viewed on a display means 12 and may also be printed on a print card by a printer 14, the print card input-output slot of which is visible in FIG. 1.

The function selected buttons 10 include a plurality of buttons which may be conveniently interfaced with control circuitry in many different ways in many different embodiments. In the present embodiment, mode selection buttons 21 through 29 are provided. The selection buttons 21-25 are respectively utilized for the routine function of power on and off, initiation of a cleaning mode, selection of a calibration mode, selection of the "backflush" mode for expelling liquid from the probe 4 and for reset. Button 26 is utilized to command a print mode when a print card is inserted in the printer 14 or otherwise to select display of calculated values as further described below. Button 27 is used to command a rinse mode which may be useful between running red blood cells and white blood cell count dilutions. The button 28 may be used to command a dual mode in which both a white blood cell count and hemoglobin measurement are made and measured values thereof generated. The button 29 is used to command red blood cell count and hematocrit measurement, i.e. generation of their measured values. This is a convenient combination since in the preferred embodiment sizing of blood cells to obtain a hematocrit measurement is performed during the red blood cell count.

In the present embodiment, the display 12 comprises two display portions 31 and 32. The display 31 includes separate display means for providing numerical indications of the arbitrary number assigned to a test sample, and what are herein referred to as the "measured values", namely WBC, RBC, HGB, and HCT. A plurality of buttons 34 may be provided to set the test number of an initial sample, and automatic indexing of the test numbers may be provided for thereafter. The display portion 32 includes a display area for displaying a calculated value, time of day or date. A plurality of buttons 36 may be provided for date set. Indicator lights 37 may indicate whether time, date, MCV, MCH, or MCHC are being displayed. By depression of the button 26, in the absence of a print card in the printer 14, the operator may set the display portion 32 to display different ones of these indications, with the indication being displayed being pointed out by one indicator light 37 being lighted next to indicia indicative of the quantity being displayed.

Figure 2:
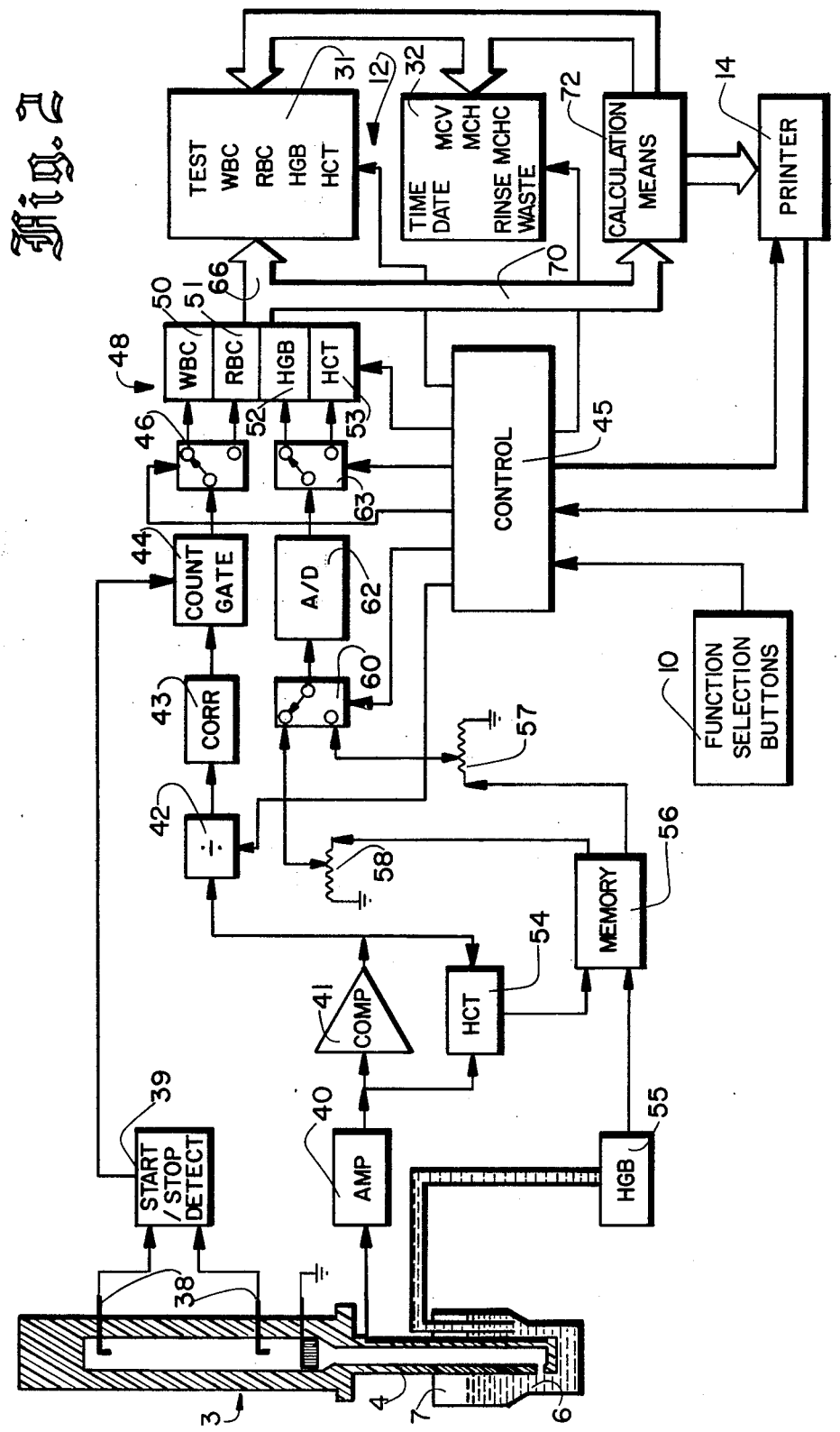
FIG. 2 is a block diagramatic representation of a circuit of the apparatus of FIG. 1.

Referring to FIG. 2, the circuitry of the hematology parameter measurement apparatus 1 is illustrated in block diagrammatic form. Further prior art details may be found in the above-cited patents whose disclosures have been incorporated herein by reference. In FIG. 2, the same reference numerals are used to denote components corresponding to those illustrated in FIG. 1. Hydraulic means (not shown) draw the dilution 6 into the sensor 3, and counts are performed as liquid rises between start and stop electrodes 38 coupled to a start and stop detection circuit 39. The sensor 3, supplied by a constant current source (not shown), provides output pulses to a buffer amplifier 40 which provides an input to a comparator 41. The comparator 41 may compare inputs provided from the buffer amplifier 40 to one threshold level for red blood cell counts and to another threshold level for white blood cell counts. Reference voltage levels are provided to the comparator 41 by conventional means (not shown). Blood cell counts are provided from the comparator 41 through a selectable ratio divider 42 to a coincidence correction circuit 43. The division ratio of the divider 42 is selected by a control circuit 45. Particular details of the control circuit 45 are a straight forward application requiring no experimentation based upon the teachings herein. Many different embodiments thereof may be provided. The control circuit 45 includes conventional timing and synchronization circuitry for commanding further operation as described below. The function selection buttons 10 are electrically interfaced to the control circuit 45. A control line is illustrated from the printer 14 to the control circuit 45 to illustrate the output of a print card presence sensor to determine whether a display or printout will be provided in response to the depression of the button 26.

The output of the coincidence correction circuit 43 is coupled by a count gate 44 connected to a switching means 46, also controlled by the control circuit 45 to provide a white blood cell count or a red blood cell count to a register means 48. The count gate 44 disables inputs to the register means 48 when counts are not being made. The register means 48 includes a plurality of multistage registers. In the present embodiment, the register means 48 includes registers 50, 51,52 and 53, each for respectively storing a digital representation corresponding to the value of white blood cell count, red blood cell count, hemoglobin and hematocrit for a sample.

A hematocrit circuit 54 is provided having an input thereto connected from the outputs of the buffer amplifier 40 and the comparator 41 for operation as described in the above-cited application to Angel and Bachenheimer. Other types of hematocrit circuitry may be used. A well-known colorimetric hemoglobin measuring system 55 is provided for providing an analog output. The hemoglobin measuring system 55 may view the dilution 6 through the sample cup 7 or may utilize a flow-through sample taken from the sample cup 7. The hematocrit circuit 54 and hemoglobin circuit 55 provide outputs to a memory circuit 56 which may comprise capacitor circuits for storing analog signals. The hemoglobin and hematocrit analog values are coupled respectively through calibration potentiometers 57 and 58 to a switching circuit 60 which connects the hemoglobin or hematocrit value to an analog to digital converter 62. The analog to digital converter 62 provides an output to a switching means 63 also connected for control by a control circuit 45 to provide a value indicative of hemoglobin to the register 52 or a value indicative of hematocrit to the register 53.

A first data bus 66 is provided for transmission of values from the register means 48 to the display 12 in proper sequence under the control of the control circuit 45. The data bus 66 is illustrated as a wide line to indicate that a plurality of bits may be transmitted in parallel. The display 12 includes conventional decoder display circuitry and the numerical indicators described above. Other utilization means (not shown) in addition to a display 12 may be provided, such as an interface for sending data to computer storage or a tape recorder. A second data bus 70 couples the register means 48 to calculation means 72 (described further with respect to FIG. 3). The calculation means 72 produces the calculated values and may provide outputs to both the printer 14 and the display 12. The data bus 70 may couple signals indicative of values of measured parameters to the printer 14 as well as to the calculation means 72. In the embodiment illustrated, the calculation means 72 comprises interface and coupling means for this purpose. It should be noted that the printer 14 includes conventional apparatus such as print card indexing means, print hammers, decoders, and drivers. As suggested above, other utilization means may be provided in place of the printer 14. However, a hard copy printout is a currently preferred vehicle for results obtained in the clinical laboratory.

Figure 3:
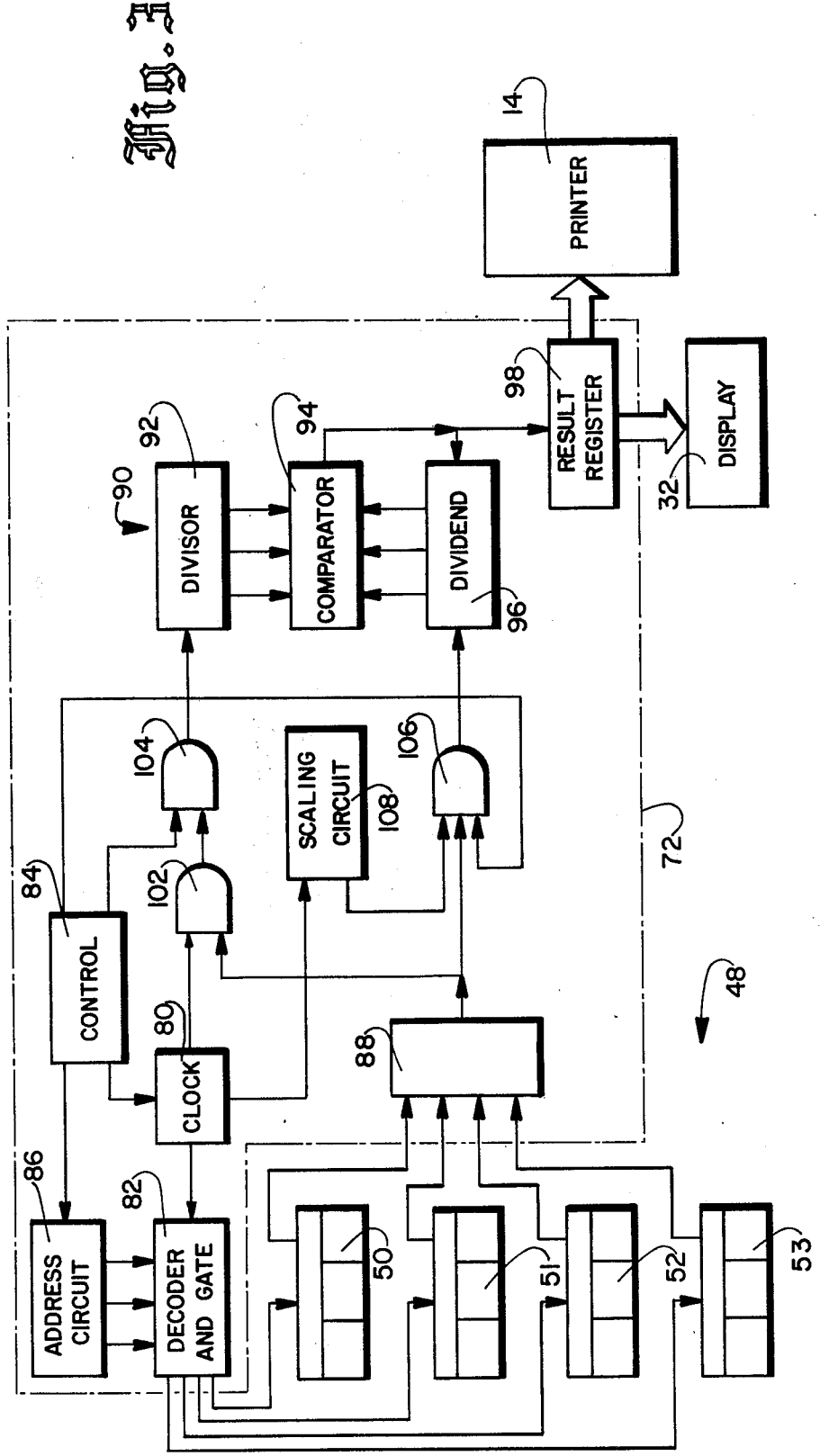
FIG. 3 is a schematic diagram of the digital data handling means for providing parameter value indications.

FIG. 3 is a schematic representation of the calculation means 72 of the present invention and its interface to the register means 48, display 12, and printer 14. Again, the same reference numerals are used to denote components corresponding to those of FIGS. 1 and 2. In the present embodiment, the values of MCV, MCH, and MCHC are referred to as the calculated values. In the present embodiment MCV is calculated as the quotient of hematocrit divided by red blood count; MCH is the quotient of the hemaglobin result divided by the red blood cell count, and mean corpuscular hemoglobin concentration, MCHC, is calculated as the quotient of the value of hemoglobin divided by the hematocrit value. Of course, in each of these calcuations, a scaling factor is applied for a normalization for such factors as sample volume size and to provide results in the proper order of magnitude.

In the calculator means 72, a clock 80 is provided which is connected to a decoder and gate circuit 82. The decoder and gate circuit 82 connects the clock 80 at a predetermined time to a selected one of the registers 50 through 53. A count sufficient to cause the register 50,51,52 or 53 to reset and return to its initial setting is produced. For example, if the registers 50 through 53 are three stage decimal counters, then a count of one thousand is provided from the clock 80. Since the registers have only three stages, the carryover when the count reaches one thousand is lost, and at the end of the count of one thousand the register returns to the same count which it had before the count of one thousand was applied thereto. The number of counts occurring after an overflow condition occurs is equal to the number of counts initially set in the one of the registers 50 through 53. For purposes of description, this operation of producing a number of counts equal to the initial setting of a register and returning the register to the initial setting is referred to as circulating a value. While rigorously speaking this is not circulation, this description is used since the value is both taken from and returned to each of the registers 50–53.

In order to determine a sequence of operation including determination of initiation of the circulation, a calculator control circuit 84 is provided which is preset to command a desired sequence and may be part of the control circuit 45. Many ways of presetting the calculator control circuit 84 will be readily apparent to those skilled in the art. The calculator control circuit 84 includes a pulse producing circuit which provides pulses at selected stages of operation to increment a counter in an address circuit 86 coupled thereto. The address circuit 86 provides counts indicative of a number which is decoded by the decoder and gate circuit 82. In correspondence with preselected counts applied thereto, the decoder and gate circuit 82 connects none or a selected one of the registers 50 through 53 to receive counts from the clock 80. Outputs from each of the registers 50–53 are provided after each register overflows and begins counting again from zero. An output indicative of overflow is provided to a gate circuit 88. The decoder and gate circuit 82 also provides reset signals to registers described below, such as at the completion of calculation of calculated values and after completion of a print mode.

The values are provided to a digital divider 90. The digital divider 90 comprises a divisor register 92, a comparator 94, and the dividend register 96. The comparator 94 produces a digital count output having a value indicative of the value of a particular calculated parameter to be produced. Results are coupled from the comparator circuit 94 to a result register 98 which separately stores each calculated value for coupling and provision to utilization means such as the display 12 or printer 14 in a conventional manner as indicated in FIG. 1.

In order to provide values to the proper components, the following circuitry is utilized. An AND gate 102 is connected to the clock 80, and has a further output connected to an AND gate 104 which in turn delivers a counting input to the divisor register 92. The AND gate 102 has a second input connected thereto from the gate circuit 88 so that provision of clock pulses through the gate 102, after the selected register 50,51,52 or 53 has reset is enabled. Thus, the divisor register will receive the same number of counts as was initially set in the particular register 50,51,52 or 53. An AND gate 106 is connected between the gate circuit 88 and the input to the dividend register 96 to enable or disable the provision of pulses thereto. A scaling circuit 108 is connected between the clock circuit 80 and another input to the AND gate 106, which is also controlled by an input from the calculator control circuit 84. The scaling circuit 108 is most conveniently a digital divider. The sequence begins after values have been provided to the register means 48 in a prior art manner.

In the preferred form, sequencing of operations by the calculator control circuit 84 is initiated in response to the inputs to the control circuit 45 from the function selection buttons 10 which command generation of the measured values. The measured values which have been generated and stored in the register means 48 must be produced to provide the measured values to the calculation means 72 via the second data bus 70. The control circuit 45 is constructed to respond to depression of the print button 26 to produce the measured values for supply to the calculation means 72. The input to the control means 45 by depression of the print button 26 is thus indicative of the command of production of measured values. After the depression of the print button 26, a calculation sequence begins in which a pulse is provided from the calculator control circuit 84 to increment the counter 86 to a preselected number which is decoded by the decoder and gate circuit 82 to connect the clock 80 to the register 50. At the same time, the calculator control circuit 84 provides an enabling input to the gate 104. The calculator control circuit 84 also provides an input to the clock 80 to initiate, in the example in which the registers 50-53 are three-stage decimal counters, a one thousand count. It is remembered that at this point, the register 50 has had a number set therein indicative of RBC. The count from the clock 80 is delivered to increment the register 50. Once the register 50 is incremented to one thousand, an output pulse is provided at the output line of the register 50 illustrated in FIG. 3 to the gate 88. The gate 88 provides an input to the AND gate 102 to enable coupling of subsequent clock pulses from the clock 80 to the divisor register 92. The remaining number of counts out of the one thousand count is equal to the value initially set in the register 50. Once the one thousand count is completed, coupling of further inputs to the divisor register 92 is inhibited.

The calculator control circuit 84 provides a pulse to increment the address counter circuit 86 such that the decoder and gate circuit 82 connects the clock circuit 80 to the illustrated input of the register 53. The calculator control circuit 84 also provides an enabling input to the AND gate 106, while the AND gate 104 remains disabled. The register 53 is incremented, and when reset, an output is provided therefrom to the gate circuit 88 so that an enabling input to the gate 106 is provided to permit coupling of clock pulses from the clock circuit 80 to the dividend register 96. The number of counts provided to the dividend register 96 is equal to the number of counts initially set in the register 53 times the scaling factor provided by the scaling circuit 108.

The count from the dividend register 96 is counted into the comparator 94 which provides an output everytime the count in the dividend register 96 and the divisor register 92 are equal. This output count also resets the dividend register 96 each time an output pulse is produced from the comparator 94. This operation is repeated until the count into the dividend register 96 is completed. The operation of the comparator 94 of acting as a register and comparator as well may be embodied, for example, through use of an RCA 4585 microcircuit chip. In this manner, the total number of pulses provided by the comparator 94 to the result register 98 has a value indicative of HCT divided by RBC, or MCV. Any remainder is left in the dividend register 96. The number of pulses provided is chosen to be sufficiently large so that resolution is not affected.

After a white blood cell dilution 6 has been supplied to the sensor 3 and the operator has depressed the button 28 (FIG. 1), a hemoglobin value has been supplied to the register 52 and a WBC value is supplied to the register 50. The calculator control circuit 84 operates similarly to produce a value of MCH. The clock 80 is connected to the register 53, and the gates 88, 102 and 104 are operated to allow a count from the clock 80 into the divisor register 92 indicative of the hematocrit value. The clock 80 is then connected by the decoder and gate circuit 82 to the register 51, and the gates 88 and 106 are operated to supply a count to the dividend register 96 indicative of the RBC value times a scaling factor. The comparator 94 then provides a value indicative of MCHC to appropriate storage locations in the result register 98. Similarly, to provide a calculated value indicative of MCH, the value in the register 51 is circulated to provide a value indicative of HGB to the divisor register 92. The register 52 is then circulated to provide a pulse count to the dividend register 96 such that the comparator 94 provides an output consisting of a pulse train having a value indicative of MCH, which value is stored in appropriate locations in the result register 98. Prior art means (not shown) may be used to blank outputs where the numerical value of the input to the divisor register 92 is below a preselected level deemed necessary for production of a reliable result, the calculated value is above a preselected threshold level indicative of an upper bound of expected results, or where no corresponding measured values are provided.

The control circuit 45 (FIG. 2) initiates transfer of values from the register means 48 to the display portion 31 (FIG. 1) of the display 12. Additionally, the depression of the print button 26 in the absence of a print card, the operator may sequentially access values as MCV, MCH and MCHC for individual display on the display portion 32. The operator may insert a print card into the printer 14 and depress the print button 26. Depression of the print button 26 initiates operation of the control circuit 45 to sequentially supply to the printer information indicative of test sample number, date and each of the measured and calculated values for which a value has been stored either in the register means 48 or the result register 98. Results are held for repeated viewing. Preferably, all registers are cleared in response to completion of the print mode, to permit registering of data for a next sample test.

What is thus provided is efficient and simplified circuitry and data handling in a hematology parameter measurement apparatus to produce and provide both measured and calculated values of parameters for a sample. The specification has been written with a view toward enabling those skilled in the art to provide innumerable modifications in the specific embodiment disclosed to provide a hematology parameter measurement apparatus constructed in accordance with the present invention.

What is claimed as new and desired to be secured by Letters Patent of the United States is:

1. In a hematology parameter measuring apparatus for producing outputs indicative of measured values including transducer means for producing signals indicative of parameter values and register means for storing indications of measured values, the improvement of means for producing calculated parameter values comprising: calculation means for calculating a calculated value as a function of measured values supplied thereto and comprising a digital divider having a dividend register and a divisor register, control means for commanding generation of calculated parameter values and means for supplying preselected measured values from said register means in a preselected sequence to said calcuation means in response to an input from said control means, wherein said register means comprises parameter registers, and said means for supplying preselected measured value comprises means for circulating a value from one of said parameter registers to one of said registers in said digital divider and means for applying a source of clock pulses for incrementing said parameter register by a number of counts to return to its original setting, means for sensing the overflow of said parameter register, and means for providing to each said register in said digital divider a multiple of the number of counts provided to the parameter register after overflow until the provision of the number of counts to the parameter register is completed, whereby said calculation means provides an output indicative of a calculated value.

2. Apparatus according to claim 1 wherein said means for circulating a value from one of said parameter registers to said divisor registers comprises means for providing to said divisor register a number of counts equal to counts occurring after overflow until the provision of the number of counts to the parameter register is completed.

3. Apparatus according to claim 2 wherein said means for circulating a value from one of said parameter registers to said dividend register comprises means for providing to said dividend register a multiple of the number of counts provided to the parameter register after overflow until the provision of the number of counts provided to the parameter register is completed which multiple is equal to a scaling factor.

4. Apparatus according to claim 1 wherein said parameter registers comprise a white blood cell count register, red blood cell count register, hemoglobin register, and hematocrit register, and wherein said means for supplying preselected measured values comprises means for accessing a value from each parameter register indicative of the parameter by which the parameter register is named.

5. Apparatus according to claim 4 wherein said means for preselected measured values comprises means for circulating a value from the red blood cell count register to the divisor register and for circulating a value dependent upon the value in the hematocrit register to dividend register whereby said digital divider provides an output indicative of mean corpuscular volume, means for circulating a value indicative of the value in the red blood cell count register to the divisor register and circulating a value based on the value in the hemoglobin register to said dividend register, whereby said digital divider provides an output indicative of mean corpuscular hemoglobin, and means for circulating a value from said hematocrit register to said divisor register and for circulating a value based on the value in the hemoglobin register to the dividend register, whereby said digital divider provides an output indicative of mean corpuscular hemoglobin concentration.

6. In a method for producing parameter values in a hematology parameter measuring apparatus comprising producing signals indicative of measured values and storing said signals in register means, the improvement of: providing calculation means comprising a digital divider having a dividend register and a divisor register for producing calculated values as a function of measured values supplied thereto, and providing in response to a command preselected ones of said measured values in a predetermined sequence to said calculation means comprising providing a first measured value from a first register to the dividend register and providing a second measured value from a second register to said divisor register, the step of providing a value from a register to said calculating means comprising providing a number of counts to said register to return said register to its original setting, sensing reset of said register and providing a multiple of the number of counts produced after reset to said calculation means, whereby a value indicative of said calculated value from said calculation means is provided.

7. The method according to claim 6 further comprising the step of providing a result register and providing the signal indicative of each calculated value to a location in a result register.

* * * * *